US010906859B2

(12) United States Patent
Veerabhadrappa et al.

(10) Patent No.: US 10,906,859 B2
(45) Date of Patent: Feb. 2, 2021

(54) ADAMANTANE-INTERCALATED LAYERED DOUBLE HYDROXIDE

(71) Applicants: Saudi Arabian Oil Company, Dhahran (SA); Durham University, Durham (GB)

(72) Inventors: Manohara Gudiyor Veerabhadrappa, Durham (GB); Hugh Christopher Greenwell, Durham (GB); Gasan Selman Alabedi, Cheshire (GB); John Adrian Hall, Dhahran (SA); Abdullah A. Al-Shahrani, Dammam (SA); Andrew Whiting, Durham (GB)

(73) Assignees: Saudi Arabian Oil Company, Dhahran (SA); Durahm University, Durham (GB)

( * ) Notice: Subject to any disclaimer, the term of this patent is extended or adjusted under 35 U.S.C. 154(b) by 119 days.

(21) Appl. No.: 16/157,542

(22) Filed: Oct. 11, 2018

(65) Prior Publication Data
US 2019/0039988 A1 Feb. 7, 2019

Related U.S. Application Data

(62) Division of application No. 15/449,207, filed on Mar. 3, 2017, now Pat. No. 10,138,199.

(60) Provisional application No. 62/309,645, filed on Mar. 17, 2016.

(51) Int. Cl.
| *C07C 61/00* | (2006.01) |
| *C07C 61/135* | (2006.01) |
| *B01J 37/08* | (2006.01) |
| *B01J 21/10* | (2006.01) |
| *B01J 23/00* | (2006.01) |
| *B01J 31/06* | (2006.01) |
| *C01F 7/02* | (2006.01) |
| *B01J 31/04* | (2006.01) |
| *B01J 35/02* | (2006.01) |
| *B01J 37/00* | (2006.01) |
| *B01J 37/03* | (2006.01) |
| *B01J 37/04* | (2006.01) |
| *C07C 51/41* | (2006.01) |
| *C09C 1/40* | (2006.01) |
| *C09C 3/08* | (2006.01) |
| *C09K 21/06* | (2006.01) |
| *B01J 21/18* | (2006.01) |

(52) U.S. Cl.
CPC ............ *C07C 61/135* (2013.01); *B01J 21/10* (2013.01); *B01J 23/007* (2013.01); *B01J 31/04* (2013.01); *B01J 31/069* (2013.01); *B01J 35/026* (2013.01); *B01J 37/0072* (2013.01); *B01J 37/031* (2013.01); *B01J 37/04* (2013.01); *B01J 37/08* (2013.01); *C01F 7/02* (2013.01); *C07C 51/418* (2013.01); *C09C 1/407* (2013.01); *C09C 3/08* (2013.01); *C09K 21/06* (2013.01); *B01J 21/18* (2013.01); *B01J 23/002* (2013.01); *B01J 35/023* (2013.01); *B01J 2231/005* (2013.01); *B01J 2531/002* (2013.01); *B01J 2531/008* (2013.01); *C01P 2002/22* (2013.01); *C07C 2603/74* (2017.05)

(58) Field of Classification Search
CPC ..... C07C 61/135; C07C 51/418; C09C 1/407; C09C 3/08; C09K 21/02; C09K 21/06; B01J 31/04; B01J 35/026; B01J 37/04; B01J 37/0072; B01J 37/031
USPC .......................................... 423/593.1–594.16
See application file for complete search history.

(56) References Cited

U.S. PATENT DOCUMENTS

| 3,342,880 A | 9/1967 | Reinhardt |
| 3,671,432 A | 6/1972 | Peters et al. |
| 4,021,371 A | 5/1977 | Petro et al. |
| 4,419,222 A | 12/1983 | Grenoble et al. |
| 4,774,212 A | 9/1988 | Drezdon |
| 4,952,748 A | 8/1990 | Alexander et al. |
| 4,956,481 A | 9/1990 | Gillaspey et al. |
| 5,021,184 A | 6/1991 | Gillaspey et al. |
| 5,073,532 A | 12/1991 | Domesle et al. |
| 5,260,495 A | 11/1993 | Forkner |
| 5,326,891 A | 7/1994 | Breuer et al. |
| 5,399,329 A | 3/1995 | Schutz et al. |

(Continued)

FOREIGN PATENT DOCUMENTS

| CA | 2594060 A1 | 6/2006 |
| CN | 105017485 A | 11/2015 |

(Continued)

OTHER PUBLICATIONS

Abdo et al., "Clay Nanoparticles Modified Drilling Fluids for Drilling of Deep Hydrocarbon Wells", Applied Clay Science, 2013, 86, 76-82, Elsevier B.V.

(Continued)

*Primary Examiner* — Steven J Bos
(74) *Attorney, Agent, or Firm* — Dinsmore & Shohl LLP

(57) ABSTRACT

Embodiments are directed to adamantane-intercalated layered double-hydroxide (LDH) particles and the methods of producing adamantane-intercalated LDH particles. The adamantane-intercalated LDH particles have a general formula defined by $[M_{1-x}Al_x(OH)_2](A)_x \cdot mH_2O$, where x is from 0.14 to 0.33, m is from 0.33 to 0.50, M is chosen from Mg, Ca, Co, Ni, Cu, or Zn, and A is adamantane carboxylate. The adamantane-intercalated LDH particles further have an aspect ratio greater than 100. The aspect ratio is defined by the width of an adamantane-intercalated LDH particle divided by the thickness of the adamantane-intercalated LDH particle.

7 Claims, 4 Drawing Sheets

(56) References Cited

U.S. PATENT DOCUMENTS

| | | |
|---|---|---|
| 5,635,457 A | 6/1997 | Van Slyke |
| 5,883,041 A | 3/1999 | Pak et al. |
| 6,096,690 A | 8/2000 | Wittenbrink et al. |
| 6,323,270 B1 | 11/2001 | Ishida |
| 6,410,635 B1 | 6/2002 | Kaylo et al. |
| 6,429,314 B1 | 8/2002 | Ishii et al. |
| 7,098,366 B2 | 8/2006 | Sigl et al. |
| 7,129,287 B1 | 10/2006 | Lee et al. |
| 7,557,063 B2 | 7/2009 | Hagemeyer et al. |
| 7,582,202 B2 | 9/2009 | Jones et al. |
| 7,918,935 B2 | 4/2011 | Park et al. |
| 8,034,867 B2 | 10/2011 | Abarca et al. |
| 8,088,349 B2 | 1/2012 | Duan et al. |
| 8,158,843 B2 | 4/2012 | Song et al. |
| 8,613,900 B2 | 12/2013 | Frei et al. |
| 8,652,994 B2 | 2/2014 | Li et al. |
| 10,105,684 B2 | 10/2018 | Veerabhadrappa et al. |
| 2002/0010520 A1 | 1/2002 | Matsubara et al. |
| 2002/0058601 A1 | 5/2002 | Jordan, IV et al. |
| 2008/0108498 A1 | 5/2008 | Duan et al. |
| 2008/0207801 A1 | 8/2008 | Ton-That et al. |
| 2010/0279848 A1 | 11/2010 | Iyi et al. |
| 2011/0237430 A1 | 9/2011 | Zhang et al. |
| 2011/0248314 A1 | 10/2011 | Takei et al. |
| 2012/0058739 A1 | 3/2012 | McKinzie, III et al. |
| 2012/0258857 A1 | 10/2012 | Pham et al. |
| 2012/0312344 A1 | 12/2012 | Delorme |
| 2012/0322694 A1 | 12/2012 | Monteiro et al. |
| 2013/0116351 A1 | 5/2013 | Querner et al. |
| 2013/0143731 A1 | 6/2013 | Li et al. |
| 2013/0172642 A1 | 7/2013 | Behrens et al. |
| 2013/0200299 A1 | 8/2013 | Mazyar et al. |
| 2013/0260990 A1 | 10/2013 | Kwon et al. |
| 2014/0113196 A1 | 4/2014 | Balaya et al. |
| 2015/0027710 A1 | 1/2015 | Miller |
| 2017/0029375 A1 | 2/2017 | Harichian et al. |
| 2017/0266642 A1 | 9/2017 | Veerabhadrappa et al. |
| 2017/0266643 A1 | 9/2017 | Veerabhadrappa et al. |
| 2017/0267620 A1 | 9/2017 | Veerabhadrappa et al. |
| 2017/0267623 A1 | 9/2017 | Veerabhadrappa et al. |
| 2017/0267910 A1 | 9/2017 | Mohammed et al. |

FOREIGN PATENT DOCUMENTS

| | | |
|---|---|---|
| EP | 1419817 A1 | 5/2004 |
| EP | 1952885 A1 | 8/2008 |
| EP | 2263976 A1 | 12/2010 |
| JP | 2012028989 A1 | 3/2012 |
| JP | 2013537877 A | 10/2013 |
| KR | 20130101038 A | 9/2013 |
| WO | 0224756 A2 | 3/2002 |
| WO | 2013007993 A2 | 1/2013 |
| WO | 2013072197 A1 | 5/2013 |
| WO | 2014037378 A1 | 3/2014 |
| WO | 2014052510 A1 | 4/2014 |
| WO | 2014080428 A1 | 5/2014 |
| WO | 2015086428 A1 | 6/2018 |

OTHER PUBLICATIONS

Abdou et al., "Evaluation of Egyptian Bentonite and Nano-Bentonite as Drilling Mud", Egyptian Journal of Petroleum, 2013, 22, 53-59, Egyptian Petroleum Research Institute.
Alvarado et al., "Preparation and Characterization of MgO Powders Obtained from Different Magnesium Salts and the Mineral Dolomite", Polyhedron, 2000, 19, 2345-2351, Elsevier Science B.V.
Baltes et al., "Synthesis of Supported Transition Metal Oxide Catalysts by the Designed Deposition of Acetylacetonate Complexes", Langmuir, 1999, 15, 5841-5845, American Chemical Society.
Bednorz et al., "Possible High Tc Superconductivity in the Ba—La—Cu—O System", Condensed Matter, 1986, 64, 189-193, Springer-Verlag.
Bernholc et al., "Bronsted Acid Sites in Transition Metal Oxide Catalysts: Modeling of Structure, Acid Strengths, and Support Effects", J. Phys. Chem., 1987, 91, 1526-1530, American Chemical Society.
Cao et al., "Mg(OH)2 Complex Nanostructures with Superhydrophobicity and Flame Retardant Effects", J. Phys. Chem., 2010, 114, 17362-17368, American Chemical Society.
Cao et al., "Ultra-High Capacity Lithium-Ion Batteries with Hierarchical CoO Nanowire Clusters as Binder Free Electrodes", Advanced Functional Materials, 2015, 25, 1082-1089, Wiley-VCH Verlag GmbH & Co.
Cavani et al., Hydrotalcite-Type Anionic Clays: Preparation, Properties and Applications, Catalysis Today, vol. 11, 1991, 173-301, Elsevier Science Publishers B.V.
Chang, et al., "Ca-Rich Ca-Al-Oxide, High-Temperature-Stable Sorbents Prepared from Hydrotalcite Precursors: Synthesis, Characterization, and CO2 Capture Capacity", ChemSusChem, 2011, vol. 4, 1844-1851, Wiley-VCH.
Chen et al., "Cu2(ATC) 6H2O: Design of Open Metal Sites in Porous Metal-Organic Crystals (ATC: 1,3,5,70Adamantane Tetracarboxylate", J. Am. Chem. Soc., 2000, 122, 11559-11560.
Chen, et al., "Preparation and Characterization of Flexible Asymmetric Supercapacitors Based on Transition-Metal-Oxide Nanowire/Single-Walled Carbon Nanotube Hybrid Thin-Film Electrodes", ACSNano, 2010, vol. 4, No. 8, 4403-4411, American Chemical Society.
Choudary et al., "Benzylation of Aromatic Compounds with Different Crystallites of Mgo", Journal of American Chemical Society, 2003, 125, 2020-2021, American Chemical Society.
Crepaldi, et al., Sorption of terephthalate anions by calcined and uncalcined hydrotalcite-like compounds, Colloids and Surfaces A: Physicochem. Eng. Aspects 211, vol. 211, No. 2-3, Jun. 4, 2002, pp. 103-114, Amsterdam, Netherlands.
Damodara et al., "Copper Nanoparticles from Copper Aluminum Hydrotalcite: An Efficient Catalyst for Acceptor- and Oxidant-Free Dehydrogenation of Amines and Alcohols", Adv. Synth. Catal., 2014, vol. 356, 189-198, Wiley-VCH.
Di Cosimo et al., "Basic Catalysis on MgO: Generation, Characterization and Catalytic Properties of Active Sites", Catalysis, 2014, 26, 1-28.
Del Arco et al., "Release studies of different NSAIDS encapsulated in Mg, AL, Fe-hydrotalcites" Applied Clay Science, vol. 42, 2009, 538-544, Elsevier B.V.
Ding, et al., "Equilibria and kinetics of CO2 absorption on hydrotalcite adsorbent" Chemical Engineering Science, 2000, vol. 55, 3461-3474, Elsevier Science Ltd.
Gardolinski et al., "Grafted Organic Derivatives of Kaolinite: I. Synthesis, Chemical and Rheological Characterization", Clay Minerals, 2005, 40, 537-546, The Mineralogical Society.
Gardolinski et al., "Grafted organic derivatives of kaolinite: II. Intercalation of primary n-alkylamines and delamination", Clay Minerals, 2005, vol. 40, 547-556, The Mineralogical Society.
Goh, et al. "Application of layered double hydroxides for removal of oxyanions: A review", Water Research (2008) pp. 1343-1368.
Guo et al., "A Comprehensive Review on Synthesis Methods for Transition-Metal Oxide Nanostructures", CrystEngComm, 2015, 17, 3551-3585, The Royal Society of Chemistry.
Haber, Jerzy, "Catalysis by Transition Metal Oxides", ACS Symposium Series, Washington D.C., 1985, Grasselli and Brazdil: Solid State Chemistry in Catalysis, American Chemical Society.
Hermoso et al., "Influence of Viscosity Modifier Nature and Concentration on the Viscous Flow Behaviour of Oil-Based Drilling Fluids at High Pressure", Applied Clay Science, 2014, 87, 14-21, Elsevier B.V.
Hsueh et al., "Preparation and Properties of LDHs/Epoxy Nanocomposites", Polymer, 2003, 44, 5275-5283, Elsevier Ltd.
Huang et al., "Controllable Preparation of Nano-MgO and Investigation of its Bactericidal Properties", Journal of Inorganic Biochemistry, 2005, 99, 986-996.
Huang et al., "Removal of NO By Reversible Adsorption on Fe-Mn Based Transition Metal Oxides", Langmuir, 2001, 17, 4997-5003, American Chemical Society.

(56) References Cited

OTHER PUBLICATIONS

International Search Report and Written Opinion pertaining to PCT/US2017/021135 dated Jun. 12, 2017.
International Search Report and Written Opinion pertaining to PCT/US2017/021478 dated May 29, 2017.
International Search Report and Written Opinion pertaining to PCT/US2017/022427 dated Jun. 12, 2017.
International Search Report dated Jul. 13, 2017, pertaining to PCT/US2017/021550, filed Mar. 9, 2017, 8 pages.
International Search Report dated Jul. 13, 2017, pertaining to PCT/US2017/022485, filed Mar. 15, 2017, 7 pages.
Itoh, et al., Nanoscale Metal Oxide Particles as Chemical Reagents. Intrinsic Effects of Particle Size on Hydroxyl Content and on Reactivity and Acid/Base Properties of Ultrafine Magnesium Oxide, Chem. Mater. 1993, vol. 5, 71-77, American Chemical Society.
Li, Jagadeesh et al., "Selective Oxidation of Alcohols to Esters Using Heterogeneous Co3O4-N@C Catalysts Under Mild Conditions", Journal of the American Chemical Society, 2013, 135, 10776-10782, American Chemical Society.
Jiancheng et al., "A New Type of Whole Oil-Based Drilling Fluid", Petrol. Explor. Develop., 2014, 41(4), 538-544, Elsevier B.V.
Johnson, Mark, "Spintronics", J. Phys. Chem. B, 2005, 109, 14278-14291, American Chemical Society.
Kanezaki, "Unexchangeable Interlayer Anions: Synthesis and Characterization of Zn/Al- and Mg/Al-Layered Double Hydroxides with Interlayer Alizarin red S", Journal of Inclusion Phenomena and Macrocyclic Chemistry, Jun. 1, 2003, pp. 89-95, https://rd.springer.com.
Kelkar et al., "Ni-, Mg- and Co-Containing Hydrotalcite-Like Materials with a Sheet-Like Morphology: Synthesis and Characterization", Microporous Materials, 1997, 10, 163-172, Elsevier Science BV.
Khan, et al., "Intercalation chemistry of layered double hydroxides: recent developments and applications", Journal of Materials Chemistry, 2002, vol. 12, 3191-3198, The Royal Society of Chemistry.
Khan, et al, The intercalation of bicyclic and tricyclic carboxylates into layered double hydroxides, Journal of Solid State Chemistry, vol. 183, No. 12, Sep. 30, 2010, pp. 2877-2885, USA.
Kim et al., "Assembly of Metal-Organic Frameworks from Large Organic and Inorganic Secondary Building Units: New Examples and Simplifying Principles for Complex Structures", J. Am. Chem. Soc., 2001, 123, 8239-8247.
Krishnamoorthy et al., "Catalytic Oxidation of 1,2-Dichlorobenzene Over Supported Transition Metal Oxides", Journal of Catalysis, 2000, 193, 264-272, Academic Press.
Kumar et al., "Effect of MgO Nanoparticles on Ionic Conductivity and Electrochemical Properties of Nanocomposite Polymer Electrolyte", Journal of Membrane Science, 2007, 300, 104-110, Elsevier B.V.
Kumbhar, et al., Reduction of Aromatic Nitro Compounds with Hydrazine Hydrate in the Presence of the Iron(III) Oxide-MgO Catalyst Prepared from a Mg-Fe Hydrotalcite Prescursor, Tetrahedron Letters, 1998, vol. 39, 2573-2574, Elsevier Science Ltd.
Kumbhar, et al., Mg-Fe Hydrotalcite as a Catalyst for the Reduction of Aromatic Nitro Compounds with Hydrazine Hydrate, Journal of Catalysis, 2000, vol. 191, 467-473, Academic Press.
Lebaron et al., "Polymer-Layered Silicate Nanocomposites: An Overview", Applied Clay Science, 1999, 15, 11-29, Elsevier Science B.V.
Li et al., "Electroreduction of Carbon Monoxide to Liquid Fuel on Oxide-Derived Nanocrystalline Copper", Nature, 2014, 508, 504-507, MacMilan Publishers.
Li et al., "Mg(OH)2@reduced Graphene Oxide Composite for Removal of Dyes From Water", Journal of Materials Chemistry, 2011, 21, 13765-13768, The Royal Society of Chemistry.
Li et al., "Positively Charged Nanosheets Derived via Total Delamination of Layered Double Hydroxides", Chem. Mater., 2005, 17, 4386-4391, American Chemical Society.
Li et al., "Preparation of Nanocomposites of Metals, Metal Oxides, and Carbon Nanotubes via Self-Assembly", J. Am. Chem. Soc., 2007, 129, 9401-9409, American Chemical Society.
Iyi, Nobuo et al., One-Pot Synthesis of Organophilic Layered Double Hydroxidees (LDHs) Containing Aliphatic Carboxylates: Extended "Homogeneous Precipitation" Method, Journal of Colloid and Interface Science, vol. 340, 2009, pp. 67-73, Japan.
First Office Action pertaining to GC patent application No. 2017-33077, dated Apr. 14, 2019, 3 pages.
First Office Action pertaining to GC patent application No. 2017-33068, dated Apr. 11, 2019, 3 pages.
Li et al., "Stable Platinum Nanoparticles on Specific MgAl2O4 Spinal Facets at High Temperatures in Oxidizing Atmospheres", Nature Communications, 2013, DOI: 10.1038/ncomms3481, MacMilan Publishers Limited.
Lima, et al., "Characterization of basic catalysts by the use of nitromethane as NMR probe molecule and reactant", Journal of Cataly, Academic Press, vol. 223, No. 1, Feb. 20, 2004, pp. 28-35, USA.
Liu et al., "Gold-Catalyzed Direct Hydrogenative Coupling of Nitroarenes to Synthesize Aromatic Azo Compounds", Angew. Chem., 2014, 126, 7754-7758, Wiley-VCH Verlag GmbH & Co.
Liu et al., "Layered Double Hydroxide Nano- and Microstructures Grown Directly on Metal Substrates and Their Calcined Products for Application as Li-Ion Battery Electrodes", Advanced Functional Materials, 2008, 18, 1448-1458, Wiley-VCH Verlag GmbH & Co.
Liu et al., "Selective and Controlled Synthesis of a- and b- Cobalt Hydroxides in Highly Developed Hexagonal Platelets", J. Am. Chem. Soc., 2005, 127, 13869-13874, American Chemical Society.
Lu et al., "Sheet-like and Fusiform CuO Nanostructures Grown on Graphene by Rapid Microwave Heating for High Li-Ion Storage Capacities", J. Mater. Chem., 2011, 21, 17916.
Ma et al., "Metal-Organic Framework Derived Hybrd Co3O4-Carbon Porous Nanowire Arrays as Reversible Oxygen Evolution Electrodes", J. Am. Chem. Soc., 2014, 136, 13925-13931, American Chemical Society.
Makhluf et al., "Microwave-Assisted Synthesis of Nanocrystalline MgO and its Use as a Bacteriocide", Adv. Funct. Mater., 2005, 15, 1708-1715, Wiley-VCH Verlag GmbH.
Meyn et al., "Anion-Exchange Reactions of Layered Double Hydroxides" Inorg. Chem. 1990, vol. 29, 5201-5207, American Chemical Society.
Mishra et al., "Effect of Nano-Mg(OH)2 on the Mechanical and Flame-Retarding Properties of Polypropylene Composites", Journal of Applied Polymer Science, 2004, 94, 116-122, Wiley Periodicals, Inc.
Miyata, Shigeo, "Physico-Chemical Properties of Synthetic Hydrotalcites in Relation to Composition", Clays and Clay Minerals, 1980, vol. 28, No. 1, 50-56, The Clay Minerals Society.
Moorhead-Rosenberg et al., "A Rapid Microwave-Assisted Solvothermal Approach to Lower-Valent Transition Metal Oxides", Inorg. Chem., 2013, 52, 13087-13093, American Chemical Society.
Mulukutla, C. Detellier, "Thermally activated Mg, Fe layered double hydroxide as reductant for nitric oxide", Journal of Materials Science Letters 1996, vol. 15, 797-799, Chapman & Hall.
Nethravathi et al., "Synthesis and Anion-Exchange Reactions of a New Anionic Clay a-Magnesium Hydroxide", Journal of Colloid and Interface Science, 2011, 354, 793-797, Elsevier Inc.
Nethrvathi, et al., Cobalt Hydroxide/Oxide Hexagonal Ring-Graphene Hybrids through Chemical Etching of Metal Hydroxide Platelets by Graphene Oxide: Energy Storage Applications, ASCNano, 2014, vol. 8, No. 3, 2755-2765, American Chemical Society.
Newman et al., "Comparative Study of Some Layered Hydroxide Salts Containing Exchangeable Interlayer Anions", Journal of Solid State Chemistry, 1999, 148, 26-40, Academic Press.
Nielsen et al., "Delamination, Synthesis, Crystal Structure and Thermal Properties of the Layered Metal-Organic Compound Zn(C12H14O4)", J. Mater. Chem., 2008, 18, 1002-1007, The Royal Society of Chemistry.
Ning et al., "Gas-Hydrate Formation, Agglomeration and Inhibition in Oil-Based Drilling Fluids for Deep-Water Drilling", Journal of Natural Gas Chemistry, 2010, 19, 234-240, Elsevier.

(56) References Cited

OTHER PUBLICATIONS

Oswald et al., "Bivalent Metal Hydroxides", Preparation and Crystal Growth of Materials with Layered Structures, 1977, 71-140.
Park et al., "Synthesis and Characterization of Al(OH)3/Polystyrene Nanocomposite Latex Particles by Emulsion Polymerization", Macromol. Symp., 2007, 247-250.
Pham et al., "A Silica-Supported Iron Oxide Catalyst Capable of Activating Hydrogen Peroxide at Neutral pH Values", Environ. Sci. Technol., 2009, 43, 8930-8935, American Chemical Society.
Poizot et al., Nano-sized transition-metal oxides as negative-electrode materials for lithium-ion batteries, Nature, 2000, vol. 407, pp. 496-499, Macmillan Magazines Ltd.
Prasanna, et al., Chromate uptake characteristics of pristine layered double hydroxides of Mg with Al, Solid State Sciences, 2008, vol. 10, 260-266, Elsevier Masson SAS.
Pupovac et al., "Cu/MgAl2O4 as Bifunctional Catalyst for Aldol Condensation of 5-Hydroxymethylfurfural and Selective Transfer Hydrogenation", ChemSusChem, 2013, 6, 2103-2110.
Qian et al., "Micropore Modification of Zeolites with Transition-Metal Oxides", Colloids and Surfaces A: Physiochemical and Engineering Aspects, 2001, 180, 311-316, Elsevier Science B.V.
Rajamathi et al., "The Many Ways of Making Anionic Clays", Proc. Indian Acad. Sci. (Chem. Sci.), 2001, 5 & 6, 671-680, Indian Academy of Sciences.
Ramirez, A.P., "Colassal Magnetoresistance", J. Phys.: Condens. Matter, 1997, 9, 8171-8199, IOP Publishing Ltd.
Rao et al., "Synthesis of Complex Metal Oxides by Novel Routes", Acc. Chem. Res., 1987, 20, 228-235, American Chemical Society.
Rao, C.N.R., "Transition Metal Oxides", Annu. Rev. Phys. Chem., 1989, 40, 291-326, Annual Reviews Inc.
Raveau, B., "Transition Metal Oxides: Promising Functional Materials", Journal of the European Ceramic Society, 2005, 25, 1965-1969, Elsevier Ltd.
Reddy et al., "Metal Oxides and Oxysalts as Anode Materials for Li Ion Batteries", Chem. Rev. 2013, 113, 5364-5457, American Chemical Society.
Stein et al., "Salt-Gel Synthesis of Porous Transition-Metal Oxides", Chem. Mater., 1995, 7, 304-313, American Chemical Society.
Reichle, Walter T., "Catalytic Reactions by Thermally Activated Anionic Clay Minerals" Journal of Catalysis, 1985, vol. 94, 547-557, Academic Press, Inc.
Sabbar, et al., "Probing the interaction between di- and tri-functionalized carboxy-phosphonic acid and LDH layer structure", Journal of Physics and Chemistry of Solids, Pergamon Press, vol. 67, No. 11, Sep. 6, 2006, pp. 2419-2429, London, England.
Schwertfeger et al., "Diamonds are a Chemist's Best Friend: Diamondoid Chemistry Beyond Adamantane", Angew. Chem. Int. Ed., 2008, 47, 1022-1036, Wiley-VCH GmbH & Co.
Schwertmann et al., "The Formation of Green Rust and its Transformation to Lepidocrocite", Clay Minerals, 1994, 29, 87-92, The Mineralogical Society.
Shukla, et al., "Stabilized a-Ni(OH)2 as Electrode Material for Alkaline Secondary Cells", J. Electrochem Soc., 1994, vol. 141, No. 11, 2956-2959, The Electrochemical Society, Inc.
Singoredjo et al., "Alumina Supported Manganese Oxides for the Low-Temperature Selective Catalytic Reduction of Nitric Oxide with Ammonia", Applied Catalysis B: Environmental, 1992, 1, 297-316, Elsevier Science Publishers B.V.
Spaldin et al., "The Renaissance of Magnetoelectric Multiferroics", Science, 2005, 309, 391-392, AAAS.
Spyrou et al., "Towards Novel Multifunctional Pillared Nanostructures: Effective Intercalation of Adamantylamine in Graphene Oxide and Smectite Clays", Adv. Funct. Mater., 2014, 24, 2841-5850, Wiley-VCH Verlag GmbH & Co.
Stankic et al., "Size-Dependent Optical Properties of MgO Nanocubes", Angew. Chem. Int. Ed., 2005, 44, 4917-4920, Wiley-VCH Verlag GmbH & Co.
Tao et al., "A redox-stable efficient anode for solid-oxide fuel cells" Nature Materials, 2003, vol. 2, 320-323, Nature Publishing Group.
Tao et al., "Synthesis and Characterization of Layered Double Hydroxides with a High Aspect Ratio", Journal of Solid State Chemistry, 2005, 179, 708-715, Elsevier Inc.
Tian et al., "Manganese Oxide Mesoporous Structures: Mixed-Valent Semiconducting Catalysts", Science, 1997, 276, 926-930.
Tokura et al., "Orbital Physics in Transition-Metal Oxides", Science, 2000, 288, 462-468.
U. Costantino, et al., Preparation and characterization of hydrotalcite/carboxyadamantan intercalation compounds as fillers of polymeric nanocomposites, Journal of Materials Chemistry, vol. 17, No. 11, Dec. 22, 2006, pp. 1079-1086.
Vidal-Michel et al., "Effect of Crystal Size on the Oxidative Dehydrogenation of Butane on V/MgO Catalysts", Journal of Catalysis, 2004, 221, 127-136, Elsevier Inc.
Walia et al., "Transition Metal Oxides—Thermoelectric Properties", Progress in Materials Science, 2013, 58, 1443-1489, Elsevier Ltd.
Wang et al., "CO2 Capture by Solid Adsorbents and Their Applications: Current Status and New Trends", Energy Environ. Sci., 2011, 4, 42-55, The Royal Society of Chemistry.
Wang et al., "Electronics and Optoelectronics of Two-Dimensional Transition Metal Dichalcogenides", Nature Nanotechnology, 2012, 7, 699-712, Macmilan Publishers.
Examination Report dated Feb. 17, 2019 pertaining to GC Application No. 2017-33078 filed Mar. 19, 2017, 3 pgs.
Office Action for Japanese Application No. 2019-500217 dated Nov. 20, 2019.
Examination Report dated May 8, 2019 pertaining to GC Application No. 2017-33063, filed Mar. 15, 2017, 5 pgs.
Wang, et al., "Synthesis of high-temperature CO2 adsorbents from organo-layered double hydroxides with markedly improved CO2 capture capacity" The Royal Society of Chemistry, 2012, vol. 5, 7526-7530, Energy Environ. Sci.
Westerhaus et al., "Heterogenized Cobalt Oxide Catalysts for Nitroarene Reduction by Pyrolysis of Molecularly Defined Complexes", Nature Chemistry, 2013, 5, 537-543.
White et al., Supported metal nanoparticles on porous materials. Methods and Applications; The Royal Society of Chemistry 2009, vol. 38, 481-494, Chemical Society Reviews.
Williams, et al., "Towards understanding, control and application of layered double hydroxide chemistry", Journal of Materials Chemistry, 2006, vol. 16, 3065-3074, Journal of Materials Chemistry.
Written Opinion dated Jul. 13, 2017, pertaining to PCT/US2017/021550, filed Mar. 9, 2017, 13 pages.
Written Opinion dated Jul. 13, 2017, pertaining to PCT/US2017/022485, filed Mar. 15, 2017, 11 pages.
Xie et al., "Low-Temperature Oxidation of CO Catalysed by Co3O4 Nanorods", Nature, 2009, 458, 746-749, Macmillan Publishers Limited.
Xu et al., "Surface Area and Thermal Stability Effect of the MgO Supported Catalysts for the Synthesis of Carbon Nanotubes", Journal of Materials Chemistry, 2008, 18, 5738-5745, The Royal Society of Chemistry.
Yao, et al., "Confined adamantane molecules assembled to one dimension in carbon nanontubes" Carbon, 2011, vol. 49, 1159-1166, Elsevier Ltd.
Yavuz, et al., "Markedly Improved CO2 Capture Efficiency and Stability of Gallium Substituted Hydrotalcites at Elevated Temperatures" Chem. Mater. 2009, vol. 21, 3473-3475, American Chemical Society.
Zhang et al., "Hydrogen Production via the Direct Cracking of Methane Over Silica-Supported Nickel Catalysts", Applied Catalysts A: General, 1998, 167, 161-172, Elsevier B.V.
Zhang et al., "Synthesis and Transformation of Linear Adamantane Assemblies Inside Carbon Nanotubes", ACS Nano, 6:10, 8674-8683.
Zhuang et al., "Comparative Study on the use of Cationic-Nonionic-Organo-Montmorillonite in Oil-Based Drilling Fluids", Applied Clay Science, 2015, 116-117, 257-262, Elsevier B.V.
Non-Final Office Action dated Jan. 5, 2018 pertaining to U.S. Appl. No. 15/453,106, filed Mar. 8, 2017.
Non-Final Office Action dated Jan. 5, 2018 pertaining to U.S. Appl. No. 15/453,180, filed Mar. 8, 2017.

(56) References Cited

OTHER PUBLICATIONS

Vittal, The Chemistry of Inorganic and Organometallic Compounds with Adamantane-Like Structures.: Polyhedron, vol. 15, No. 10, pp. 1585-1642 (1996).

Non-Final Office Action dated Apr. 23, 2018 pertaining to U.S. Appl. No. 15/449,347, filed Mar. 3, 2017.

U.S. Non-Final Office Action dated May 25, 2018, pertaining to U.S. Appl. No. 15/449,207.

Office Action pertaining to U.S. Appl. No. 15/453,056 dated Jul. 10, 2018.

International Search Report and Written Opinion dated Aug. 10, 2018 pertaining to International Application No. PCT/US2018/030399, 15 pages.

J. Costantino et al., "Preparation and characterisation of hydrotalcite/carboxyadamantane intercalation compounds as fillers of polymeric nanocomposites", Journal of Materials Chemistry, 2007, vol. 17, pp. 1076-1086, www.rsc.org/materials, UK.

Makoto Ogawa, et al., "Hydrothermal Synthesis of Layered Double Hydroxide-Deoxycholate Intercalation Compounds", Chemical Materials, 2000, vol. 12, pp. 3253-3255, USA.

Kumar et al., "Sonochemical Synthesis and Characterization of Nanometer-Size Transition Metal Oxides from Metal Acetates", Chem .Mater., 2000, 12, 2301-2305, American Chemical Society.

Zhao et al., "Carbon Nanowire Made of a Long Lineal Carbon Chain Inserted Inside a Multiwalled Carbon Nanotube", Physical Review Letters, 2003, vol. 90, No. 18, 187401-1-187401-4, The American Physical Society.

Office Action dated May 26, 2020 pertaining to U.S. Appl. No. 15/966,312, filed Apr. 30, 2018, 9 pgs.

Saliba, D. et al. "Kinetics of intercalation of fluorescent probes in magnesium-aluminum layered double hydroxide within a multiscale reaction-diffusion framework" in Philosophical Transactions Royal Soc. A 374: 20160138 (Aug. 2016), pp. 1-14, downloaded May 20, 2020 from http://dx.dox.org/10.1098/ rsta.2016.0138. (Year: 2016).

Office Action dated Jun. 12, 2020 pertaining to U.S. Appl. No. 15/971,634, filed May 4, 2018, 8 pgs.

Office Action pertaining to Korean Application No. 10-2018-7029901 dated Apr. 10, 2020, 6 pgs.

U.S. Notice of Allowance and Fee(s) Due dated Aug. 26, 2020 pertaining to U.S. Appl. No. 15/966,312, filed Apr. 30, 2018, 84 pgs.

ively relate to high aspect ratio layered double hydroxide materials, and specifically relate to high aspect ratio layered double hydroxide materials and methods for preparation.

ADAMANTANE-INTERCALATED LAYERED DOUBLE HYDROXIDE

CROSS-REFERENCE TO RELATED APPLICATIONS

This application is a divisional application of U.S. patent application Ser. No. 15/449,207 filed Mar. 3, 2017, which claims the benefit of U.S. Provisional Application Ser. No. 62/309,645 filed Mar. 17, 2016.

BACKGROUND

Field

Embodiments of the present disclosure generally relate to layered double hydroxide materials, and specifically relate to high aspect ratio layered double hydroxide materials and methods for preparation.

Technical Background

The synthesis of supported metal or metal-oxide catalysts is of great industrial importance in heterogeneous catalysis. High activity, high selectivity, and long catalyst life are desirable characteristics of any industrial catalyst. Catalyst materials may be produced from layered double hydroxides (LDHs). LDHs, which are also known as anionic clays, are inverse charge analogues of the widely used aluminosilicate cationic clays in their structure and properties. Though a number of methods exist to prepare metal oxide particles in general, oxides obtained by decomposing LDHs have several advantages compared to oxide particles obtained by synthetic methods such as wet impregnation/solid state preparation. Specifically, LDHs may provide a simple, cost effective and environmentally suitable way to achieve a homogeneous distribution of metal ions at the atomic level. In order to make use of LDH layers for various applications, one needs to be able to exfoliate or delaminate these layers. Since carbonate LDHs are thermodynamically more stable, it is difficult to exchange it for other ions or to exfoliate LDH layers where carbonate is the charge balancing ion. As a result, these materials have limited usage. There have been attempts to prepare high aspect ratio non-carbonated LDHs starting from carbonate LDH; however, this approach has multiple steps and is cumbersome.

SUMMARY

In accordance with the background previously presented, ongoing needs exist for LDH materials having high aspect ratios.

Embodiments of the present disclosure are directed to LDHs produced with the high symmetry adamantane ion, which mediates the growth of high aspect ratio platelets. Moreover, due to its organophilic nature, adamantane can be exfoliated in organic solvents. Thus, these LDH layers can be used in various applications as previously mentioned. The embodiments of the present disclosure are directed to high aspect ratio non-carbonated LDHs, which use just one equivalent of anion salt. Moreover, these LDHs provide process improvements in that they enable "one pot" synthesis, and less washing (including no washing) at the end of the reaction due to the use of metal hydroxides as starting materials and just one equivalent of anion. The materials formed also have desirable properties once calcined.

According to one embodiment, a method for preparing adamantane-intercalated layered double-hydroxide (LDH) particles is provided. The method comprises adding to an aqueous solution a first precursor and a second precursor to form an initial mixture, where the first precursor is $Al(OH)_3$ or $Al_2O_3$, and the second precursor is a hydroxide $M(OH)_2$ or an oxide MO, where M is a metal of oxidation state +2. The initial mixture has a M/Al molar ratio of from 1 to 5 or a solid loading of less than 10 weight % solids, based on a total weight of the initial mixture. The method further comprises adding to the initial mixture an amount of adamantane to form a reaction mixture having an Al/adamantane molar ratio of from 0.5 to 2, and heating the reaction mixture to produce the adamantane-intercalated LDH particles, where the adamantane-intercalated LDH particles have aspect ratios greater than 100. The aspect ratio is defined by the width of adamantane-intercalated LDH particles divided by the thickness of the adamantane-intercalated LDH particles.

According to another embodiment, an adamantane-intercalated layered double-hydroxide (LDH) material in the form of adamantane-intercalated LDH particles is provided. The adamantane-intercalated LDH particles comprise a general formula defined by $[M_{1-x}Al_x(OH)_2](A)_x \cdot mH_2O$, where x is from 0.14 to 0.33, m is from 0.33 to 0.50, M is chosen from Mg, Ca, Co, Ni, Cu, or Zn, and A is adamantane carboxylate. The adamantane-intercalated LDH particles further comprise an aspect ratio greater than 100. The aspect ratio is defined by the width of an adamantane-intercalated LDH particle divided by the thickness of the adamantane-intercalated LDH particle.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1B:
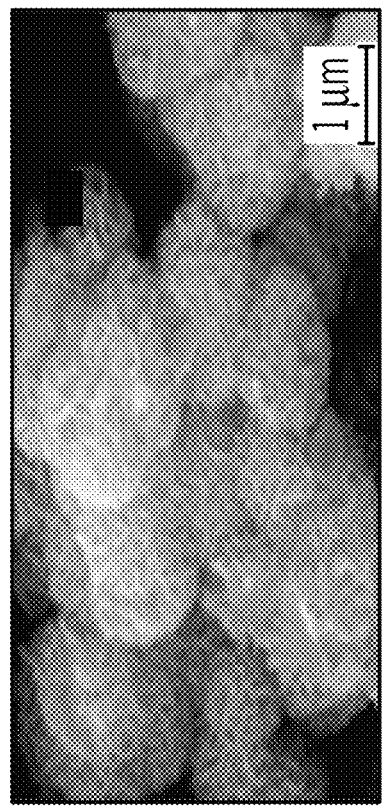
FIG. 1B is an SEM image of an Mg/Al—$CO_3$ LDH produced via co-precipitation.

The dispersion of active reduced metal or metal-oxide particles on a stable support is a complex and laborious process. To achieve this, one needs to consider various parameters such as the synthesis conditions, nature of the support and appropriate ways of dispersing/distributing active catalyst on the support. Among the metal/metal oxide supported catalysts, the $Cu/ZnO/Al_2O_3$ system and metal/metal oxide (Pt, Pd, Rh and Au) systems supported on various supports (alumina, silica, and carbon) have great industrial importance. These catalytic systems are known to have potential for catalyzing industrially important reactions such as synthesis of methanol, water gas shift reaction, desulfurization of petrochemical streams, photochemical/electrochemical splitting of water, and photochemical/electrochemical reduction of carbon dioxide into useful chemicals, for example.

Reference will now be made in detail to embodiments of adamantane-intercalated layered double-hydroxide (LDH) particles with high aspect ratios and the methods of producing them. Specifically, the adamantane-intercalated LDH particles have aspect ratios greater than 100. As defined, the aspect ratio is defined by the width of the LDH particle divided by the thickness of the LDH particle. As defined, an aspect ratio below 10 is considered low, an aspect ratio less than 100 is considered medium, and an aspect ratio of 100 or greater is considered a high aspect ratio. The LDH particles may be calculated from the SEM images. For example, referring to the embodiment of FIG. 2B, it is clear that the layered particles have large surface area, but lack thickness, thereby resulting in a high aspect ratio. Additionally, Atomic Force Microscopy (AFM) may be utilized to measure the width and thickness of the LDH particles and determine an aspect ratio.

Methods for preparing adamantane-intercalated LDH particles may include the step of adding to an aqueous solution a first precursor and a second precursor to form an initial mixture. In one embodiment, the aqueous solution may consist essentially of water. The first precursor may comprise $Al(OH)_3$ or $Al_2O_3$. The second precursor may include a metal containing compound, for example, a hydroxide $M(OH)_2$ or an oxide MO, where M is a metal of oxidation state of +2. While various other metals are also contemplated, the M may be chosen from Mg, Ca, Co, Ni, Cu, Zn, or combinations thereof. In one or more embodiments, the second precursor may include $Mg(OH)_2$, $Ca(OH)_2$, $Co(OH)_2$, $Ni(OH)_2$, $Cu(OH)_2$, $Zn(OH)_2$, or combinations thereof. In further embodiments, the second precursor is $Mg(OH)_2$ or MgO. In one example, the second precursor is $Mg(OH)_2$ and the first precursor is $Al(OH)_3$.

Moreover, in further embodiments, the initial mixture may have a M/Al molar ratio of 1 to 5, or 1 to 3. Furthermore, the initial mixture may have a solid loading of less than 10 weight % solids, based on a total weight of the initial mixture, or a solids loading or less than 5 weight % solids.

Subsequently, the method includes adding to the initial mixture an amount of adamantane to form a reaction mixture having an Al/adamantane molar ratio of from 0.5 to 2. In one or more additional embodiments, the Al/adamantane molar ratio may be from 0.8 to 1.2, or may be 1 to 1. Various adamantane sources are contemplated. In one embodiment, the adamantane may be added in the form of a carboxylic acid. Optionally, the reaction may be stirred.

Generally, LDHs for conversion to mixed metal oxide catalysts are prepared with inorganic guest anions, which may be easily removed under thermal treatment. When using an organic anion, such as carboxylic acid functionalized adamantane, improved properties for LDHs may be achieved. Adamantane has a structure characterized by high symmetry ($T_d$), is free from intra-molecular strain and, as a result, is extremely thermodynamically stable. At the same time, adamantane can be chemically functionalized. Adamantane has a melting point of 270° C. and it slowly sublimes even at room temperature. Adamantane is poorly soluble in water, but readily soluble in hydrocarbons.

Without being bound by theory, the use of thermally stable adamantane is as a structure directing agent, which allows for preferential growth of the LDH in the a and b crystallographic directions over the c crystallographic axes. This results in the high aspect ratio particles observed. Moreover, the use of hydrothermal synthesis and metal hydroxide precursors carefully controls the growth conditions in terms of pH and kinetics.

Next, the method includes heating the reaction mixture to produce the adamantane-intercalated LDH particles, where the adamantane-intercalated LDH particles have aspect ratios greater than 100. As defined, the adamantane-intercalated LDH particles means the adamantane is inserted into the LDH particle matrix. In further embodiments, the aspect ratio of the adamantane-intercalated LDH particles is greater than 125, or greater than 150, or greater than 200. Moreover, the adamantane-intercalated LDH particles have a particle diameter of 2 to 12 µm, or from 5 to 10 µm. The heating step may occur at a reaction temperature from 110° C. to 180° C. for a reaction time of 12 hours to 48 hours, or from 130° C. to 170° C. for a reaction time of 20 hours to 30 hours.

The largest group of the LDH family of materials includes positively charged metal hydroxide layers having the composition $[M^{II}_{1-x}M^{III}_x(OH)_2]^{x+}$ or $[M^I_x M^{III}_{1-x}(OH)_2]^{x+}$ ($M^I$=Li; $M^{II}$=Mg, Ca, Co, Ni, Zn; $M^{III}$=Al, Cr, Fe; $0.14 \leq x \leq 0.33$). The positive charge on the layers is balanced by anions present in the interlayer. The anions give rise to the name anionic clays. One group of anionic clays includes materials having a general formula $[M^{II}_{1-x}M^{III}_x(OH)_2]$ $(A^{n-})_{x/n} \cdot mH_2O$ or $[M^I_x M^{III}_{1-x}(OH)_2]^{x+}(A^{n-})_{x/n} \cdot mH_2O$ (m=0.33-0.50), where A is an anion such as nitrate or halogen.

The adamantane-intercalated LDH particle may have a general formula $[M_{1-x}Al_x(OH)_2](A)_x \cdot mH_2O$, where x is from 0.14 to 0.33, m is from 0.33 to 0.50, M is chosen from Mg, Ca, Co, Ni, Cu, or Zn and A is adamantane carboxylate.

LDHs with high aspect ratios play a role in the development of oxygen barriers in packaging, as fillers in nanocomposite materials, and as flame-retardants, amongst others. For all these applications, high aspect ratio platelets that can be readily dispersed in a polymer matrix are desirable, but not easily attainable. Anion (charge and symmetry of the anion) plays a crucial role in nucleation and growth of LDH crystals. The carbonate ion, which is ubiquitous in nature, has $D_3h$ symmetry matching well with interlayer symmetry of the LDH and also it has higher charge density compared to other anions. As a result, LDHs prefer carbonate ions over other ions and this mediates the ordered stacking of layers. The SEMs of FIGS. 1A and 1B shown Mg/Al-carbonate LDHs produced via anion exchange and co-precipitation respectively.

In contrast to the present embodiments, LDHs are conventionally prepared by a co-precipitation technique, in which a homogeneous mixed solution of metal salts is added to another solution containing sodium hydroxide and an excess of the guest anion to be incorporated. LDHs obtained from this method always show crystallites with submicron size due to rapid multiple nucleation and crystallization events. Co-precipitated crystals may have aspect ratios of approximately 1-10 or less. This indicates that the crystals have narrow breadth and grow preferentially along the c axis. This is a reflection of the high supersaturation of both anion and cation and the rapid nucleation of many crystals in the mixed zone in the reactor.

Figure 1A:
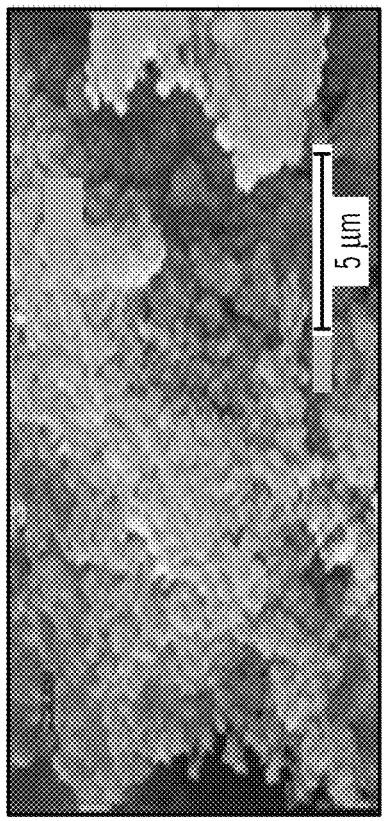
FIG. 1A is a Scanning Electron Microscopy (SEM) image of an Mg/Al—$CO_3$ LDH produced via anion exchange.
Figure 2B:
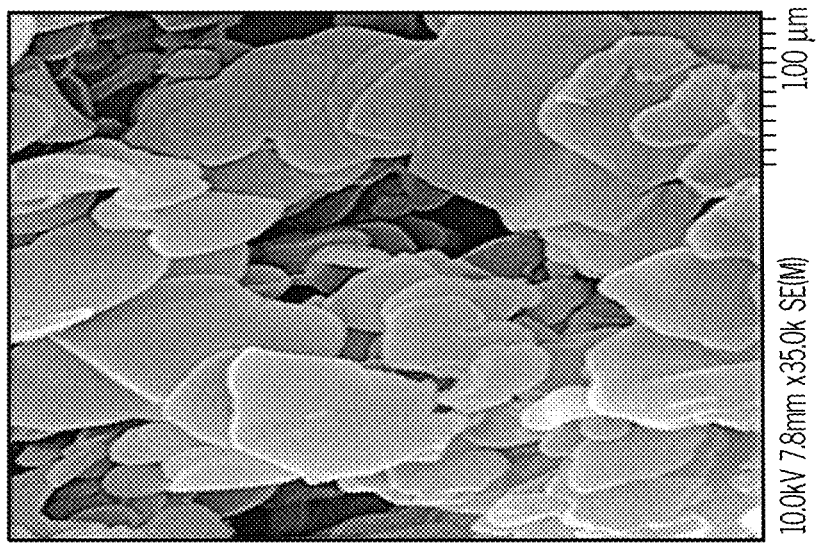
FIGS. 2A and 2B are SEM images of different magnifications of an Mg/Al-adamantoate LDH produced in accordance with one or more embodiments of the present disclosure.
Figure 2A:
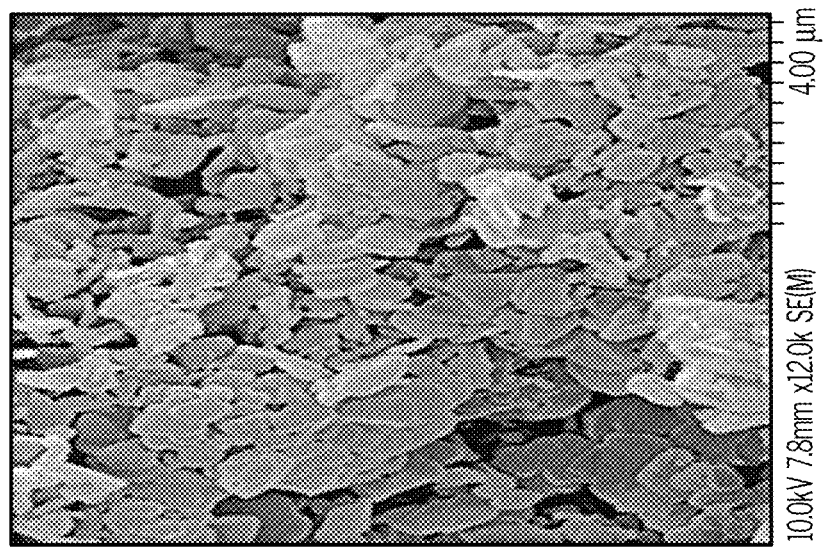

For illustration, SEM images of Mg/Al—$CO_3$ LDH samples prepared by co-precipitation and anion exchange method are provided in FIGS. 1A and 1B. As shown, these particles are irregular thick agglomerates. As a result of this thickness, the aspect ratio is low for the Mg/Al—$CO_3$ LDH samples. In contrast, the SEM micrographs of Mg/Al-adamantoate LDH produced as shown in FIGS. 2A and 2B depict sheet like layers having much less thickness than the Mg/Al—$CO_3$. In light of these low thicknesses, these Mg/Al-adamantoate LDH particles have a high aspect ratio.

EXAMPLES

The described embodiments will be further clarified by the following example.

Example 1

Preparation of Layered Double Hydroxide

In one typical preparation, a 5 weight % solution of $Mg(OH)_2$ was prepared by dissolving 5 grams (g) of $Mg(OH)_2$ in 95 g of de-ionized water. To this 3.36 g of $Al(OH)_3$ was added to give a Mg/Al molar ratio of 2. Then, 9.31 g of adamantane carboxylic acid was added to the same solution (Al/adamantane molar ratio=1) and the resultant reaction mixture was stirred vigorously for 1 hour at room temperature. After this, the solution was transferred to a Teflon lined autoclave and heated at 150° C. for 24 hours (h). The pH of the initial reaction mixture and final filtrate was measure and was found to be 9.5 and 8.6 respectively. In another set of experiments, the above procedure was repeated by taking Mg/Al molar ratio of 5. After the reaction was over, the products were washed thoroughly with water and dried at 65° C.

For comparison, an Mg/Al—$NO_3$ LDH (Mg/Al molar ratio=2) was synthesized by a more conventional ammonia precipitation method starting from metal nitrates.

Figure 3:
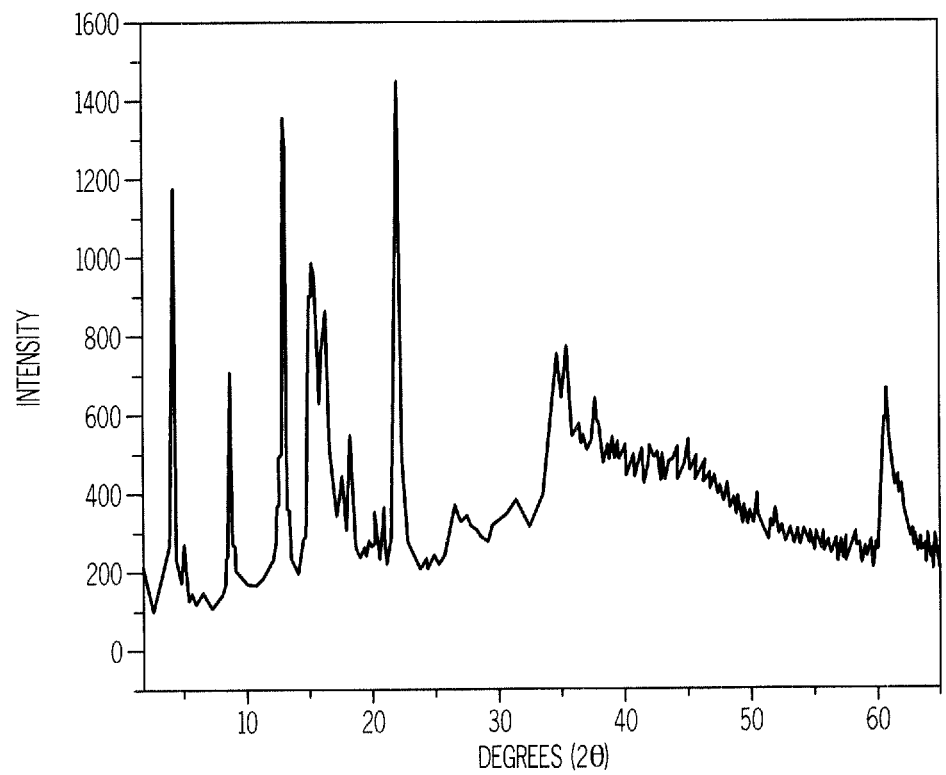
FIG. 3 is a Powder X-Ray Diffraction (PXRD) graph of a Mg/Al-adamantoate LDH in accordance with one or more embodiments of the present disclosure.
Figure 4:
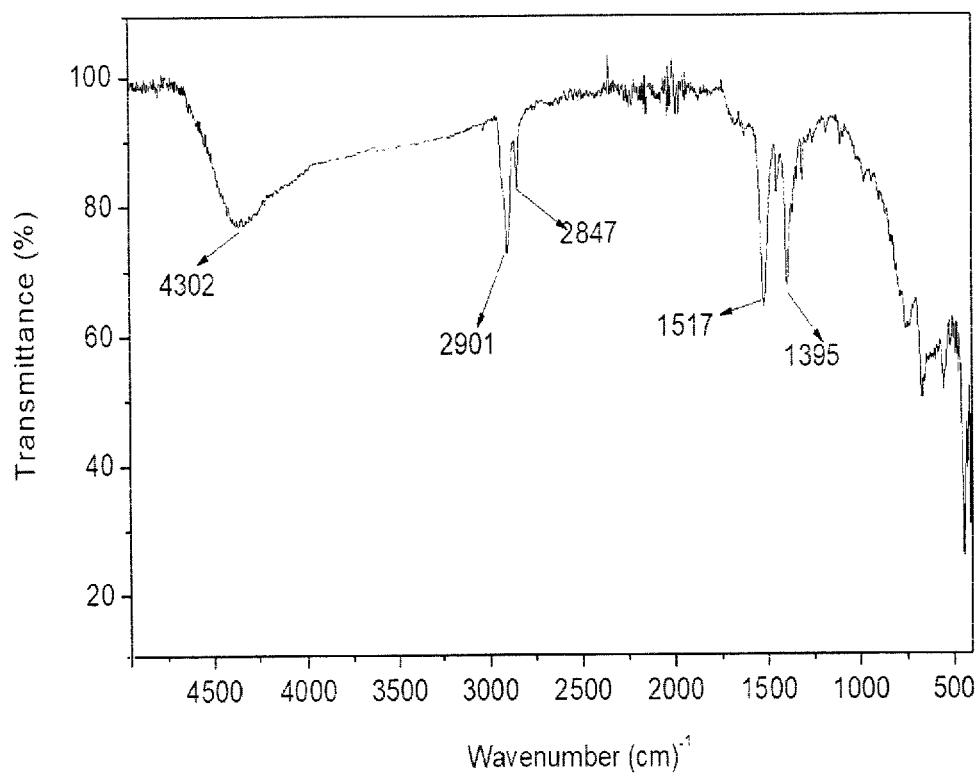
FIG. 4 is an Infrared (IR) Spectroscopy graph of a Mg/Al-adamantoate LDH in accordance with one or more embodiments of the present disclosure.

The PXRD pattern of the as-synthesized LDH is given in FIG. 3, and shows that the basal reflection (001) at 20.84 Å corresponds to a bilayer arrangement of adamantane ions in the interlayer. The submultiples of (001) are seen at higher 2θ values. Intercalation of adamantoic acid was further characterized with IR spectra as shown in FIG. 4. The vibrations at 1517 $cm^{-1}$ and 1395 $cm^{-1}$ correspond to antisymmetric and symmetric stretching vibrations of the $COO^-$ group. The vibrations at 2901 $cm^{-1}$ and 2847 $cm^{-1}$ are for the C—H vibrations. The 4302 $cm^{-1}$ vibration is due to hydrogen bonding of layer metal hydroxide groups with intercalated water molecules in the interlayer.

Figure 5:
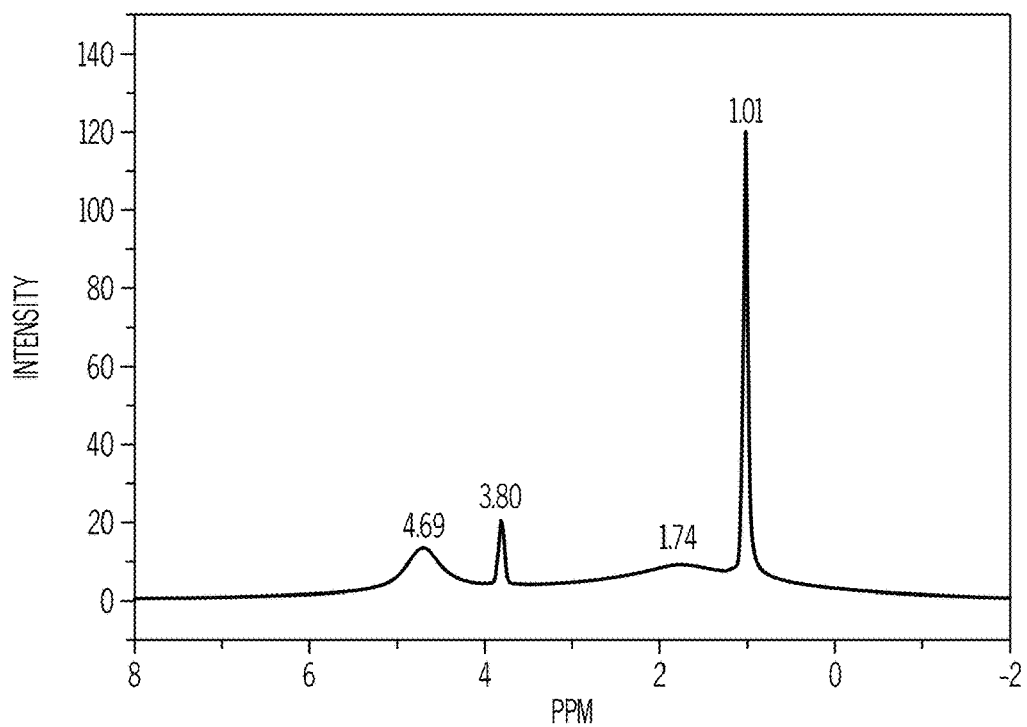
FIG. 5 is a graph of the $^1H$ solid-state Nuclear Magnetic Resonance (NMR) spectra of a Mg/Al-adamantoate LDH in accordance with one or more embodiments of the present disclosure.
Figure 6:
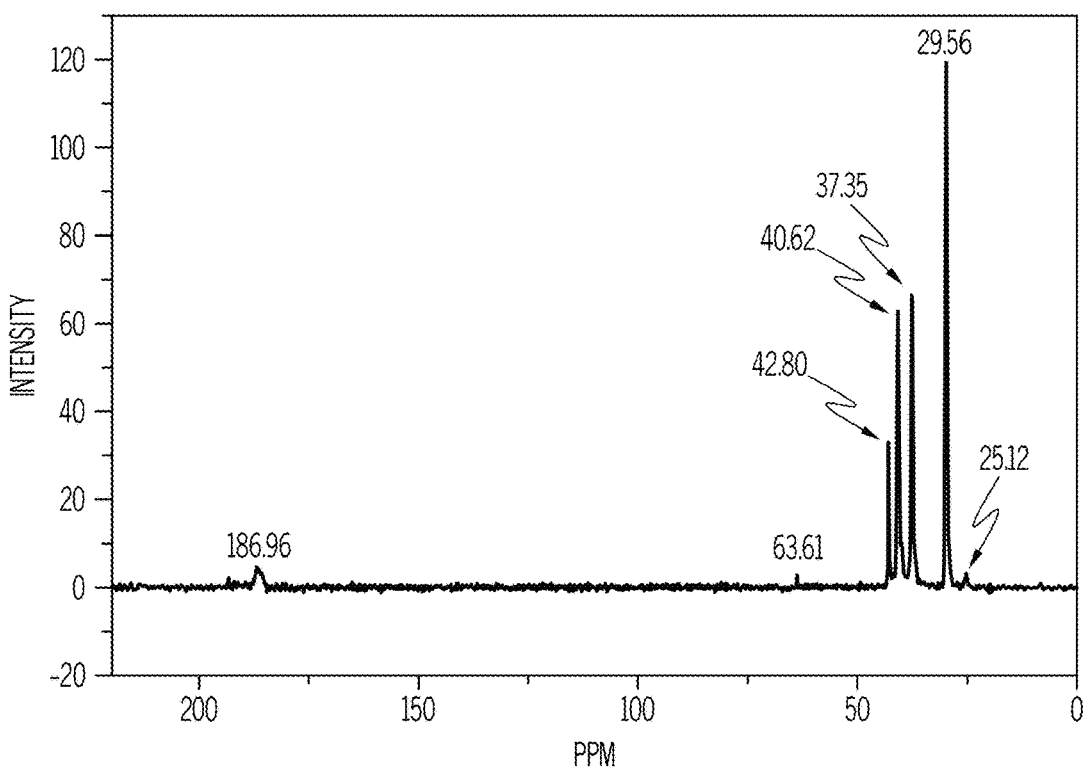
FIG. 6 is a graph of the $^{13}C$ solid-state NMR spectra of a Mg/Al-adamantoate LDH in accordance with one or more embodiments of the present disclosure.

The $^1H$ and $^{13}C$ solid-state NMR spectra of Mg/Al-adamantoate LDH were recorded and are given in FIGS. 5 and 6, respectively. The 4 sharp peaks in the $^1H$ spectra of FIG. 5 at lower ppm values are due to the hydrogens present in the adamantane ring. The peaks at 3.8 ppm and 4.8 ppm are due to the hydrogens of the intercalated water and metal hydroxide respectively. Referring to FIG. 6, the $^{13}C$ NMR spectra of Mg/Al-adamantoate shows 4 peaks at 29.5 ppm, 37.3 ppm, 40.6 ppm and 42.8 ppm, which are due to 4 different carbons present in the adamantane molecule. The peak at 186.98 ppm is due to the carbon of the carboxylate group. Scanning Electron Microscope (SEM) images of as-synthesized LDH show platelet morphology typical of layered materials (FIGS. 2A and 2B).

It will be apparent to those skilled in the art that various modifications and variations can be made to the embodiments described herein without departing from the spirit and scope of the claimed subject matter. Thus it is intended that the specification cover the modifications and variations of the various embodiments described herein, provided such modifications and variations come within the scope of the appended claims and their equivalents.

What is claimed is:

1. An adamantane-intercalated layered double-hydroxide (LDH) material in a form of adamantane-intercalated LDH particles, where the adamantane-intercalated LDH particles comprise:

a general formula defined by $[M_{1-x}Al_x(OH)_2](A)_x \cdot mH_2O$, where x is from 0.14 to 0.33, m is from 0.33 to 0.50, M is chosen from Mg, Ca, Co, Ni, Cu, or Zn, and A is adamantane carboxylate; and an aspect ratio greater than 100, the aspect ratio defined by a width of an adamantane-intercalated LDH particle divided by a thickness of the adamantane-intercalated LDH particle.

2. The adamantane-intercalated LDH material of claim 1 where M is Mg.

3. The adamantane-intercalated LDH material of claim 1 where the aspect ratio is greater than 125.

4. The adamantane-intercalated LDH material of claim 1 where the aspect ratio is greater than 150.

5. The adamantane-intercalated LDH material of claim 1 where the aspect ratio is greater than 200.

6. The adamantane-intercalated LDH material of claim 1 where the adamantane-intercalated LDH particles have a particle diameter of 5 to 10 μm.

7. The adamantane-intercalated LDH material of claim 1 where the adamantane-intercalated LDH particles have characteristic peaks in an IR spectra at 1517 $cm^{-1}$, 1395 $cm^{-1}$, 2901 $cm^{-1}$, 2847 $cm^{-1}$, and 4302 $cm^{-1}$.

* * * * *